United States Patent [19]

Berna Tejero et al.

[11] Patent Number: 5,157,158

[45] Date of Patent: * Oct. 20, 1992

[54] ALKYLATION OF AROMATIC HYDROCARBONS

[75] Inventors: Jose L. Berna Tejero, Boadilla de Monte; Alfonso Moreno Danvila, Algeciras, both of Spain

[73] Assignee: Petroquimica Espanola, S.A. Petresa, Madrid, Spain

[*] Notice: The portion of the term of this patent subsequent to Sep. 8, 2009 has been disclaimed.

[21] Appl. No.: 746,120

[22] Filed: Aug. 15, 1991

Related U.S. Application Data

[63] Continuation of Ser. No. 387,289, Jul. 28, 1989.

[51] Int. Cl.$^5$ .............................................. C07C 39/06
[52] U.S. Cl. ..................................... 568/628; 585/467
[58] Field of Search ................. 585/467; 568/628,626

[56] References Cited

U.S. PATENT DOCUMENTS

| | | | |
|---|---|---|---|
| 3,374,182 | 3/1968 | Young | 502/64 |
| 3,992,467 | 11/1976 | Striddle | 585/467 |
| 4,197,413 | 4/1980 | Kaeding et al. | 585/468 |
| 4,205,189 | 5/1980 | Young et al. | 568/468 |
| 4,469,908 | 9/1984 | Buress | 585/467 |
| 4,499,320 | 2/1985 | Garces | 585/467 |
| 4,587,370 | 5/1986 | DeGraff | 585/450 |
| 4,891,448 | 1/1990 | Garces et al. | 568/628 |

FOREIGN PATENT DOCUMENTS 83970 6/1983 European Pat. Off. .

Primary Examiner—Anthony McFarlane
Attorney, Agent, or Firm—Darby & Darby

[57] ABSTRACT

A process is described for the alkylation of benzene (in general, aromatic hydrocarbons), with $C_2$–$C_{20}$ mono-olefins in the presence of an aluminum-magnesium silicate catalyst, to give linear alkylbenzenes of detergent range, basic product in the manufacture of biodegradable detergents.

The process is continuously carried out in a fixed bed, the alkylation taking place in a liquid phase.

The alkylation catalyst is mainly made up of aluminum silicate and/or magnesium silicate and is conveniently modified to improve its activity and attain an adequate yield and selectivity in the alkylation for the desired product.

28 Claims, No Drawings

ALKYLATION OF AROMATIC HYDROCARBONS

This is a continuation of application Ser. No. 387,289, filed Jul. 28, 1989.

This invention refers to a process of alkylation of aromatic hydrocarbons with $C_2$–$C_{20}$ monoolefins in the presence of an aluminum-magnesium silicate as catalyst to produce alkylaromatic compounds.

DESCRIPTION OF THE BACKGROUND

The processes for alkylation of aromatic compounds with a Friedel-Crafts type catalyst, for example, aluminum trichloride, boron trifluoride, sulfuric acid, hydrofluoric acid, phosphoric acid and the like, are known and used commercially. However, the above described catalysts have the disadvantage of causing corrosion of the materials of the process aside from causing problems of elimination of waste products.

Aside from the mentioned catalysts, the use of activated clay and solid zeolite catalysts has been suggested as catalysts suitable for the alkylation of aromatic compounds to form aromatic alkylated compounds. When using solid zeolite catalysts, two modes of operation have been basically described. First, the catalyst can be used as a powder pap in the liquid reagents. This process has disadvantages since it generally requires operating discontinuously instead of continuously and besides it requires expensive filtering and centrifuging units to separate the catalyst from the desired product and from the unreacted compounds. A more commercially feasible technique implies the use of a fixed bed reactor which contains relatively large catalyst particles, through which the reagents are continuously made to pass.

U.S. Pat. No. 4,459,426 proposes the use of zeolite as the alkylation catalyst of benzene with light $C_2$–$C_4$ olefins. Due to the reduced sized of the zeolite pores, around 10 Å, they do not allow the diffusion of heavy molecules, thus, the alkylation in the presence of said catalysts can only be carried out with light olefins.

U.S. Pat. No. 3,849,507 proposes the use of a clayish material, activated with mineral acids and subsequently made into pellets, for the alkylation of benzene with olefins with 4 to 8 carbon atoms per molecule.

U.S. Pat. No. 4,046,826 uses a natural or synthetic triooctahedral clay, hectorite type, interchanged with metallic cations, for the alkylation of benzene with heavy olefins, basically 1-dodecene. Chemically, the hectorite used consists of a hydrated magnesium silicate, with small contents of fluorine, lithium, and other metals, the latter in interchange position. The product, be it natural or synthetic, should be previously interchanged with metallic cations which have a high electronegativity, as $Al^{3+}$ or $Cr^{3+}$ in order to obtain a catalyst with important catalytic activity.

On the other hand, European patent application 83,970 uses for the alkylation of benzene with light olefins, a clay in which pillars of alumina have been anchored inside its laminar structure, as catalyst.

U.S. Pat. No. 3,671,601 developed by C. L. Sanderson and E. S. Sauer and assigned to the Continental Oil Company, describe the production and purification of crude aromatic alkylate (more specifically alkylbenzene) by reaction of an olefin material or a chlorinated paraffin with an aromatic compound (more specifically benzene) in the presence of aluminum halide as a catalyst. In general, the catalyst used is $AlCl_3$, either in a pure form or, more frequently, in a complex form, with different organic groups. Likewise, the catalyst may be used in a fluidized form or as a fixed bed on a solid support. This process has the problem that it requires a laborious and costly subsequent operation of separation and purification of the obtained alkylbenzene.

Fishel in his U.S. Pat. No. 3,417,148 refers to an alkylation process in which an aromatic compound, for example, benzene, toluene, xylene, etc. is alkylated with an olefin, using a catalyst that consists of crystalline aluminosilicate chemically combined with metallic subfluoride. The compounds which act as olefin include: olefins, acetylene hydrocarbons, alcohols, esters, ethers, and alkyl halides. The metallic subfluorides are described as aluminum monofluoride, silica difluoride, etc.

Another alkylation process is described in the U.S. Pat. No. 4,070,407 of Haag, which implies alkylation of aromatic compounds which takes place by reaction in which the aromatic hydrocarbons react with an alkylation or transalkylation agent, using a catalyst formed by a crystalline aluminosilicate zeolite. Olefins, alkyl halides and alcohols are adequate alkylation agents as well as alkyl hydrocarbons and aromatic polyalkyl.

In U.S. Pat. No. 3,585,253 of S. K. Huang assigned to Monsato Co. there is reference to an integrated process which includes the separation of paraffins, dehydrogenation of paraffins to olefins, alkylation of aromatics with olefins and sulfonation of detergent alkylate. The alkylation phase takes place by reaction of benzene with a mixture of hydrocarbon containing olefins, in the presence of anhydrous HF as the catalyst. The ratio of benzene to olefin is approximately 6:1 and that of HF to olefin is 18:1. The reaction temperature is 50° C. Subsequently the desired alkylbenzene product, aside from the HF, benzene and paraffins which have not reacted are separated from the effluent.

In the process developed by E. R. Fenske, U.S. Pat. No. 3,494,971, assigned to U.O.P. Company the production of a monoalkylated aromatic hydrocarbon adequate for the production of a detergent product is described. The alkylation between the aromatic compound and the linear monoolefin hydrocarbon takes place in successive steps and uses hydrogen fluoride as a catalyst, which may be fresh and/or regenerated, depending on the different steps of the process. The feeding of linear hydrocarbon (10 to 15 carbon atoms per molecule) is made up of a mixture of an excess (90%) of non-dehydrogenated linear hydrocarbons, along with a minor olefin fraction (10%) with approximately 95% monoolefins and 5% diolefins.

The aromatic compound which reacts with the hydrocarbon stream, in the presence of HF as the catalyst, is benzene in molar excess over the monoolefin fraction. Two phases are obtained as the reaction production, the one which contains the alkylation catalyst and the ones that contains the hydrocarbons, from which are separated on the one part, the HF catalyst which is partly regenerated and on the other part, the unreacted benzene, which is recycled again, the present paraffins (which do not react) and some HF, aside from the desired product, the alkylbenzene. This monoalkylated aromatic hydrocarbon has a bromine index lower than 30 and, typically between 10 and 20.

Many other patents described similar alkylation processes with different types of reagents and which use these same cited catalysts, of the Friedel-Crafts type: hydrofluoric acid (U.S. Pat. No. 3,494,970, U.S. Pat. No. 3,830,865), aluminum trichloride (U.S. Pat. No.

3,631,123, U.S. Pat. No. 3,674,885, U.S. Pat. No. 3,703,559), etc., as well as the clay and zeolite type.

It has been known for quite some time that clay materials have catalytic properties with regard to different organic liquid compounds and that this property varies depending on the type of clay. Over the last 25 years big success has been attained in the production of clay catalysts for the process of cracking oil and for the manufacture of gasolines. At the present time, pillared type clays are being researched as selective catalysts for a certain type of processes (polymerizations) and reactions or large molecules (steroids, antibiotics, etc.) with molecule sizes suitable for their interstices, larger than those of other types of clays and zeolites.

Likewise, it has been described that different materials which contain acidic catalytic points are useful as catalysts of the reaction between aromatic hydrocarbons and different alkylation agents, such as olefins and alkyl halides. See for example: Kirk-Othmer Encyclopedia of Chemical Technology, 2nd. Ed., Vol. 1, pages 882-901 (1963); "Alkylation of benzene with dodecene -1 catalyzed by supported silicotungstic acid," R. T. Sebulsky and A. M. Henke, Ind. Eng. Chem. Process Res. Develop., Vol 10, No. 2, 1971, pages 272-279; "Catalysis by metallic halides, Iv. Relative efficiencies of Friedel-Crafts catalysts in the isomerazation of cyclohexane-methyl-cyclopentane, Alkylation of benzene and polymerazation of styrene," G. A. Russell, J. Am. Chem. Soc., Vol. 81, 1959, pages 4834–4838.

The use of different modified clays has also been proposed as catalysts for different reactions catalyzed by acids, such as alkylation isomerization and the like. See for example the different U.S. Pat. Nos.: 3,665,778, 3,665,780, 3,365,347, 2,392,945, 2,555,370, 2,582,956, 2,930,820, 3,360,573, 2,945,072 and 3,074,983. The last patent describes the use of hectorite clay as a catalyst. Other references which describe the use of clays as catalysts are the following: "Acid Activation of some bentonite clays," G. A. Mills, J. Holmes and E. B. Cornelius, J. Phy. & Coll. Chem., Vol. 54, pages 1170-1185 (1950); "H-ion catalysis with clay," N. T. Coleman and C. Mc Auliffe, Clays and Clay Minerals, Vol. 4, pages 282-289 (1955) "Clay minerals as catalysts," R. H. S. Robertson, Clay Mineral Bulletin, Vol. 1, No. 2, pages 47-54 (1948); "Catalytic decomposition of glycerol by strata silicates," G. F. Walker, Clay Minerals, Vol. 7, page 111-112 (1967); "Polymerization of styrene with interchanged cation aluminosilicates," T. A. Kusnitsyna and V. M. Brmolko, Vysokomol. Soedin, Ser. B 1968, Vol. 10, No. 10, pages 776-9 See Chem Abstracts 70:20373 x (1969); "Reactions catalyzed by minerals. Part I. Styrene polymerization," D. H. Solomon and M. J. Rosser, J. Applied Polymer Science, Vol. 9 1261-1271 (1965.)

As it can be easily seen from the above, there is abundant research under way to obtain catalysts and new processes and more efficient ones for the production of alkylated aromatics, from olefins and aromatic compounds.

Consequently, an improved process for the alkylation of aromatic compounds is an object of the present invention.

Additionally, it is an object of the present invention to furnish a process of alkylation of benzene with $C_2$-$C_{20}$ range monoolefins, using a solid catalyst of a suitable porosity and activity, in a fixed bed, which provides important advantages over the normal methods, which use liquid catalysts or else solid ones of different structure and features.

Other objects and advantages of the invention will be inferred from the following description.

DESCRIPTION OF THE INVENTION

The present invention consists of a process for producing alkylated aromatic hydrocarbons by reacting a molar excess of aromatic hydrocarbon, preferably benzene, with $C_2$-$C_{20}$ range monoolefins and preferably $C_8$-$C_{16}$ in a reactor under alkylation conditions which include the presence of a liquid phase and an alkylation catalyst in a fixed bed, basically made up of hydrated aluminum silicate and magnesium silicate.

The process is carried out continuously and the feed to the reactor consists of a mixture of benzene and moisture free olefin, in a benzene/olefin molar ratio from 30:1 to 1:1; the olefins may be diluted with n-paraffins of the same $C_8$-$C_{16}$ range, in a ratio from 1:1 to 1:20.

The product of the alkylation reaction is subsequently fractionated, separating the following fractions: (1) a fraction of aromatic hydrocarbon (benzene), (2) a substantially pure linear monoalkylbenzene fraction (3) a fraction of heavy alkylates and (4) a fraction of n-paraffins. The fractions of benzene and n-paraffins are recycled to the process subsequently.

The reaction temperature is from 150°–300° C., the liquid hourly pressure is 10–50 kg/cm$^2$ and the space velocity (LHSV) is from 0.5–10 hr$^{-1}$. The catalyst is, preferably, an aluminum and/or magnesium silicate, with a specific surface area higher than 100 m$^2$/g and a pore diameter less than 50 Å, conveniently modified in their acid centers to improve their catalytic activity and alkylation selectivity, reaching conversion of 90–100%, with a selectivity of 80–95% for the linear alkylbenzene.

The catalyst is cyclically regenerated by passing alternating currents of paraffins and alcohols, its catalytic effectiveness being very long-lasting.

The elimination of water from the raw materials, as well as from the catalyst and from the washing products thereof is important.

This alkylation process is applicable to other types of aromatic compounds, such as for example, toluene, xylene, phenol, etc., also to alkylbenzenes and to many other alkylating agents, such as alkyl halides, alcohols, esters, acetylene hydrocarbons, etc. to give a large variety of alkylaromatic compounds (and dialkylaromatic compounds), though it is especially indicated to obtain detergent range linear alkylbenzenes.

DETAILED DESCRIPTION OF THE INVENTION

The present invention consists of a process for the alkylation of aromatic hydrocarbon with an olefin compound, which comprises the separation of the alkylation reaction product in (1) an aromatic fraction (2), a monoalkylaromatic fraction, (3) a heavy alkylaromatic fraction and (4) a paraffin fraction, the recycling to the process of aromatic and paraffin fractions, the separation of an essentially pure monoalkylaromatic compound of the reaction product, using as an alkylation catalyst an activated clay basically made up of aluminum silicate and magnesium silicate on a fixed bed and which is cyclically regenerated in a semi-continuous manner.

Preferably, the monoalkylaromatic compound obtained as a reaction product in the process consists of $C_8$-$C_{16}$ detergent range linear monoalkylbenzene basic product in the manufacture of synthetic biodegradable detergents.

In a representative alkylation process of this invention a carbon steel tubular reactor equipped with temperature and pressure control mechanisms, in which the catalyst has been introduced in the form of a fixed bed is used. In this reactor, and at the adjusted operating conditions of the process, the alkylation reaction takes place in liquid phase when the feed is passed through it continuously at a constant speed or, alternatively, at a variable speed. The feed enters the reactor in a liquid phase through the top part and consists of a flow of a mixture of paraffins and olefins to which another current of aromatic hydrocarbon is added, in turn, in part fresh and in part coming from the fractionation recycling.

Normally, the aromatic hydrocarbon and the paraffin-olefin mixture are contacted in a benzene/olefin molar ratio of about 30:1 to 1:1, especially, from about 25:1 to 1:1 and, preferably, from about 20:1 to 1:1. This molar ratio maximizes the life of the catalyst while it prevents the forming of excesses of polyalkylated aromatics. Normally, the stream of the paraffin-olefin mixture has a paraffin/olefin ratio, given in weight percentage, from about 1:1 to 20:1, especially about 16:4 to 19;1 and, preferably, from about 17:3 to 19:1.

In accordance with this invention, the aromatic hydrocarbon is alkylated with $C_2$-$C_{20}$ range linear olefins and preferably $C_8$-$C_{16}$, the paraffins being the ones that accompany them, in the mixture, also of linear nature and of this same range. Other types of suitable compounds for alkylating the aromatic hydrocarbon include alkyl halides alcohols, acetylene hydrocarbons, esters, ethers and other olefins. The aromatic hydrocarbons that are suitable for this purpose are those aromatic hydrocarbons which can be alkylated under the prescribed reaction conditions. Suitable aromatic hydrocarbons include benzene, toluene and xylene, as well as other alkylbenzenes, such as monoalkyl benzenes having an alkyl moiety with 8 to 16 carbon atoms. The preferred aromatic hydrocarbon is benzene.

The temperatures which are suitable for use in this process are those temperatures which initiate the reaction between the aromatic hydrocarbon and the particular olefin used to selectively produce the desired aromatic-alkyl compound. Generally suitable temperatures to be used are from 150° C. to 300° C., especially from 180° C. to 230° C. Keeping the reaction temperature in this range reduces the formation of undesired by-products, such as polyalkylated aromatic hydrocarbons and increases the yield of the reaction in the desired monoalkylated aromatic compounds. The heating of the reactor is achieved by an electric tubular furnace.

The pressure range of the process is limited in its top margin by the vapor pressure of the most volatile reaction component, benzene, at the operating temperature, so that the reaction takes place in the liquid phase. According to this, the suitable pressures for this process are, preferably, approximately above 10 kg/cm$^2$ but should not exceed 50 kg/cm$^2$. An especially desirably pressure range is from 15 kg/cm$^2$ to 40 kg/cm$^2$.

The liquid hourly space velocity ranges from 0.5 to 20.0 hr$^{-1}$, especially, from 0.5 to 10.0 hr$^{-1}$ and, preferably, from 0.5 to 4.0 hr$^{-1}$. It should be taken into account that the combination of temperature and pressure used, is such that the alkylation reaction essentially takes place in liquid phase.

In a process in liquid phase to produce alkylaromatic compounds, the catalyst is continuously washed with reagents, thus preventing the formation of coke precursors on the catalyst. This causes very small amounts of carbon formation on said catalyst, and thus the life of each catalyst cycle is extensive, when it is compared with an alkylation process in a gas phase, process in which the coke formation and the deactivation of the catalyst are an important problem.

As a result of the presence of minor components in the feed (isoparaffins, diolefins, polyolefins, etc.) and due to the different types of reactions, small amounts of byproducts such as heavy alkylates diphenylalkanes, dialkylbenzenes), branched alkylbenzenes, polymers, tetralins, indans, etc. are produced. However, the aluminum-magnesium clay used as a catalyst in a fixed bed in this invention, has a high degree of selectivity for the production of alkylaromatic compounds in general and more specifically for the desired product of linear alkylbenzene. The degree of conversion of the reaction is practically total, being a minimum of 95%, likewise having a selectivity of the same for linear alkylbenzene which is very high, generally from 80-95%, with some percentages in heavy alkylates in the neighborhood of 2-20% by weight and, more frequently, from 1-8% by weight, this corresponding to some similar percentages of dialkylbenzene as well as of diphenylalkane. As to the branched alkylbenzenes percentages in the neighborhood of 2 to 10% by weight and, more frequently, in the neighborhood of 4-8% are obtained.

This alkylation reaction product is separated into four fractions using conventional separation techniques. The four fractions comprise (1) an aromatic fraction, preferably benzene, (2) a monoalkylated aromatic fraction, preferably linear monoalkylbenzene, (3) a heavy alkyl-aromatic fraction, generally diphenylalkanes and dialkylbenzenes and (4) a n-paraffin fraction, preferably of detergent range. The fraction which comprises the monoalkylated aromatic compound, preferably linear monoalkylbenzene, is recovered from the mixture which constitutes the reaction product using conventional techniques. A portion of the recovered aromatic fraction preferably benzene is mixed with another portion of fresh benzene and is recycled again to the alkylation reactor, first mixing with the stream of paraffins and olefins. According to this invention, a suitable ratio of recycled benzene to fresh benzene is about 75-95% by weight of recycled benzene and about 5-25% by weight of fresh benzene and, especially, about 85-95% by weight of recycled benzene and 5-15% by weight of fresh benzene. The n-paraffin fraction undergoes a step of catalytic dehydrogenation to n-monoolefins, until the suitable percentage of the above mentioned paraffin/oleffin ratio for the feed which is, preferably, from about 17:3 to 19:1 by weight and, subsequently, it is mixed with the benzene current (fresh and recycled) until the suitable benzene/olefin ratio plus paraffin, indicated above for the feed which is, preferably, from about 20:1 to 1:1 by weight and which implies the optimal ratio for the life an activity of the catalyst.

The alkylation catalyst used in the present invention consists of a solid provided with an important surface acidity standing out among them, preferably, aluminosilicates and magnesium silicates, be they natural or synthetic, which have a high surface acidity.

The main parameter which determines the catalytic activity for the alkylation reaction is the surface acidity, the higher the latter the higher the conversion, for some determined operating conditions. However, it is not convenient to use catalysts with an excessively high acidity, since though they have a noteworthy activity, the selectivity towards monoalkylaromatic compounds drops drastically, upon undesired secondary reactions of polyalkylation, oligomerization, isomerization, etc. This would make the process rather expensive, therefore, a situation of optimal compromise between a high activity catalyst but which has, in turn, an acceptable selectivity towards the desired monoalkylaromatic hydrocarbons, must be reached.

Aside from having active catalytic centers of a moderately acidic nature, which act catalyzing the alkylation reaction the catalyst is characterized by having a high specific surface (determined by the BET method of adsorption of nitrogen at the temperature of liquid nitrogen) higher than 80 $m^2/g$ and, preferably, higher than 100 $m^2/g$, therefore, there is a large available surface on which the reaction can take place, which justifies the notable activity which the catalyst demonstrates. This is likewise characterized, due to the structure thereof, by having a high microporosity, higher than 0.2 $cm^3/g$, the large part of the surface of the catalyst corresponding to pores with a diameter smaller than 60 Å and, preferably, smaller than 50 Å, therefore the formation of large size molecules (oligomers, heavy molecules, etc.) is prevented by the reduced size of the pores of the catalyst, thus contributing to increase the selectivity of the process for the formation of linear alkylbenzene.

Particularly important is the high percentage meso and macropores with diameters larger than 50 Å. This permits an easy diffusion, of the products as well as of the reagents, inside the catalyst, even when they are made up of voluminous hydrocarbon molecules with a heavy molecular weight, therefore, they result especially suitable for alkylation processes of benzene with heavy olefins, with more than ten carbon atoms per molecule. The distribution of pore sizes with a high percentage of meso and macropores is obtained by incorporating in the catalyst materials with a high porosity, among which are the following: sepiolite, paligorskite, diatomaceous earth, perlite, silica, alumina, etc. These materials may be added to the catalyst during the preparation thereof, or else be ready present in the natural starting mineral, thus the addition thereof is not necessary.

Among the synthetic products usable as catalysts, we can cite amorphous silice-alumina and zeolites, preferably synthetic faujasites (zeolite X or Y.) Among the natural products zeolites of natural clays can be preferably used, standing out among the zeolites clinoptilolite, mordenite, chabazite and eryonite, and among the clays kaolinite, sepiolite, paligorskite, bentonite, montmorrillonite, hectorite, smectite, saponite, chlorite, halloysite and ylite.

Besides, the catalyst can be made up of a mixture of two or more compounds of the above mentioned ones, in which one of them acts as a binder and to provide the catalyst with the suitable porosity and specific surface area, which permits a good diffusion of products and reagents inside the catalyst.

For the purpose of strenghthening the activity of the catalyst, this can be subjected to different treatments, among which ionic interchange treatments, treatments with acids and treatments of impregnation with different salts or acids turn out to be especially advantages. Among the ionic interchange treatments, a notable increase in the activity of the catalyst is in its natural state, by salts of the following cations: $Al^{3+}$, $Cr^{3+}$, $H^+$, rare earths and $NH_4^+$. The interchange with a salt of this last cation must be followed by a thermal treatment so that ammonia ($NH_3$) is given off and the catalyst remains in its proton form ($H^+$).

Likewise, especially active catalysts are obtained by treatment with different acidic agents of said materials. Among said acids are the following: sulfuric acid, nitric acid, hydrochloric acid, perchloric acid, phosphoric acid, acetic acid, etc. Likewise, improvements are obtained in the activity of the catalyst, by impregnation of the same with the listed acids, with fluorine salts or with salts containing some of the following metals: aluminum, chrome, manganese, wolfram or rare earths.

The catalyst used in the process of the present invention can be used in its natural state as well as in its synthetic state, in granular form, though, to facilitate its use in the reactors of a fixed bed, it is more convenient to shape it into spherical, cylindrical agglomerated pellets, which can be obtained by conventional processes of pastille formation, extrusion, agglomeration, pelleting or any other conventional process. In the shaping of the catalyst the binders normally used in catalysts can be used, among which stand out, metallic hydroxides or oxides, preferably, aluminum oxide, silica-alumina and natural clays. However, the catalysts used and particularly the natural products, can be used in granular form.

After the shaping step, the catalyst is dried to a temperature between 60° to 120° C. preferably between 100° and 110° C. and finally it is calcined to a temperature between 200° and 600° C., preferably between 300° and 500° C.

The regeneration of the catalyst is done cyclically, by alternating and successive washing with paraffins and alcohols the catalyst bed, in cycles lasting for a period of time within the range of about 2 to about 8 hours.

Said regeneration of the catalyst is carried out at a temperature of 150°–300° C. and, preferably, 180°–230° C. and at a liquid hourly space velocity of 1–10 $hr^{-1}$ and, preferably, from 1–4 $hr^{-1}$.

The mixture of solvents coming from the regeneration washing of the catalyst contains polymeric products and it is subjected to successive decantation and fractionated distillation operations to separate the different components, being subsequently recycled to the regeneration process.

An advantage of the present invention, lies in an alkylation process in a liquid phase, in which the catalyst is continually washed by the reagents, thus preventing the deposition of coke precursors, such as polymers, on the surface of said catalyst, which tend to deactivate and shorten the catalytic life cycle, giving thus a much longer life of the catalyst in the process.

An important advantage of the present invention with regard to other similar alkylation processes which also use clayish type catalysts is the use of a natural and/or synthetic type catalyst which, as has been stated above, has specific particular features: catalytic activity, selectivity, degree of conversion, surface acidity, specific surface and porosity, which the catalyst itself intrinsically has already of which can be acquired or strengthen by means of using different conventional treatments: ionic interchange, treatment with acids, impregnation with different salts or acids, etc. and which make it especially suitable for use thereof in alkylation processes of benzene (aromatic hydrocarbons) $C_{10}$–$C_{14}$ paraffin monoolefins, to give detergent range linear alkylbenzenes (alkylaromatics), with a high yield, purity and selectivity.

Another advantage of the present invention consists in that the alkylation process with heterogeneous catalysis in a fixed bed reactor, upon using a solid catalyst insoluble and unmixable with the reagents and with the reaction products, there are practically no problems of separation and purification thereof, nor of recovery of residual products, in contrast with other type of non-solid catalysts. Thus, when hydrofluoric acid is used as a catalyst (minimum purity required 95%), fluorides, among others, are produced as reaction byproducts by addition of the hydrofluoric acid to the olefins, just like the polymers, by polymerization of said olefins. These polymers are soluble in the acid phase and blacken and impurify the hydrofluoric acid, being necessary to regenerate it and to separate said polymers by fractionation. In this same way, the recovered benzene contaminated by the fluorides which accompany it should be purified for its subsequent recycling to the process. The hydrocarbons and the hydrofluoric acid are not miscible, but they become saturated from one phase into the other and both must also be separated, purified and regenerated.

When the catalyst used in the alkylation process is aluminum trichloride (or aluminum tribromide,) the problems which arise are also numerous, such as the ones derived from the necessary purification and separation of the crude reaction product, contaminated by residual catalyst and by other byproducts (alkyl chlorides or alkyl bromides), hydrochloric acid or hydrobromic acid, etc.) undesirable odors in the reaction product, costly and difficult regeneration of the catalyst, formation of an undesirable color in subsequent processes (sulfonation) with the alkylbenzene obtained, etc.

All these problems effect the investment price and complicate the process and thus the use of the catalyst in fixed bed in the alkylation process object of the present invention, avoids and eliminates to a large degree all these inconveniences.

Another outstanding advantage of the present invention lies in the use, in the alkylation process of a novel method of recovery of the catalyst, which is carried out cyclically, by means of passing alternating and successive currents of paraffin and alcohols, thus obtaining a very long-lasting catalytic effectiveness.

Another important advantage of the present invention will regard to other alkylation processes which use acid type corrosive and dangerous catalysts, such as HF (very corrosive in the presence of certain proportions of water, $H_2SO_4$, etc. is the use of harmless and non-corrosive easy-to-use catalysts, such as the ones pointed out in the description of this invention, thus avoiding personal risks and the use of costly materials and equipment such as specially alloys, as well as the use of special protective material and equipment, etc. which are necessary when corrosive and strongly acidic products are used. Obviously, this implies for the case which is the object of this invention a large savings, a lowering of costs and high competitivity and simplicity in the process and handling.

Still another advantage of the present invention is an alkylation process with a clayish type catalyst which has high activity and selectivity for the production of detergent range linear alkylbenzenes and which yields very pure reaction products, with contents of undesirable byproducts, in amount as well as in diversity, considerably lower than other similar alkylation processes, in which Friedel-Crafts type catalysts are used: $AlCl_3$, HF, etc. This is due to the special features of the process in fixed bed object of this invention, as well as those of the catalyst used, which has a structural nature and porosity suitable to prevent the production of certain types of byproducts (oligomers and polymers, large molecules, alkyl indans, alkyl tetralins, other heavy aromatics, etc.) and favor the production of the desired alkylaromatic compounds.

Finally, another advantage of the present invention with regard to other similar competitive processes is the elimination of the inconveniences which arise in these processes, derived from the formation of incondensable products in the process, consisting of light gases (hydrogen, methane, ethane, etc.) which in the case of the invention with which we are dealing do not take place due, among other causes, to the different nature and features of the alkylation catalyst used in this process.

The process of this invention described above is illustrated hereafter with some specific examples which, however, have no restrictive nature on said invention.

EXAMPLES

Example 1

Benzene is alkylated with $C_{10}$–$C_{14}$ detergent range linear olefins to produce linear monoalkylbenzene of an identical range.

The alkylation reaction is carried out continuously in a tubular pressure reactor made out of carbon steel and with down flow system, with a length of 600 mm an inside diameter of 24.3 mm, an outside diameter ratio of 25.4 mm and a height/inside diameter of 25. The reactor is provided with two thermowells for temperature control, located at one-third and two-third from its height respectively, measured from the bottom. The heating of the feed and of the reactor is obtained by an electric tubular furnace, the reactor likewise having pressure, flow and temperature control mechanisms.

In this reactor 270 g of catalyst occupying a volume of 250 cm$^3$ are introduced and placed in the form of a fixed bed. The catalyst consists of an alumino-silicate with a silica content of 61% and an alunina content of 16% by weight respectively. It is shaped in granular form and the grain size is 30–60 mesh.

The feed of the reactor enters into a liquid phase through its top part coming out in a liquid phase through the bottom. It is formed by two streams one of benzene consisting of a mixture of recycled benzene and fresh benzene and another formed by a mixture of paraffins and olefins. The composition and percentage thereof are specified in detail hereafter in Table I.

TABLE I

| Composition of the feed | % by weight |
| --- | --- |
| Benzene | 46 |
| Fresh benzene | 2.6 |
| Recycled benzene | 43.4 |
| Paraffins and olefins | 54 |
| Paraffins | 48.9 |
| Olefins | 5.1 |

The distribution of the paraffins and olefins mixture, is the following:

|  | % by weight |
| --- | --- |
| n-C10 | 12.0 |

-continued

| | % by weight |
|---|---|
| n-C11 | 36.3 |
| n-C12 | 29.4 |
| n-C13 | 21.7 |
| n-C14 | 0.6 |

The reaction conditions of the process are summarized hereafter in Table II.

TABLE II

| Benzene/olefin molar ratio | 20 |
|---|---|
| Pressure | 35 kg/cm$^2$ |
| Temperature | 220° C. |
| Liquid Hourly Space velocity | 1 hr$^{-1}$ |

The amount of olefins at the entrance of the reactor is controlled by measuring the bromine number of the feed stream and the conversion at the outlet of the reactor is likewise controlled by determination of the bromine number in said outlet stream.

The results shown in Table III were obtained in the cited conditions.

TABLE III

| Conversion | 100% |
|---|---|
| (Bromine number at the entrance | 5.1) |
| (Bromine number at the outlet | 0) |
| Selectivity | |
| Linear alkylbenzene | 85.2% by weight |
| Branched alkylbenzene | 7.4% by weight |
| Heavy alkylbenzene | 7.4% by weight |
| Dialkylbenzene | 3.7% by weight |
| Diphenylalkane | 3.7% by weight |
| Life of the catalyst (duration of the experiment; 300 hrs. equivalent to 278 ml of feed/g of catalyst) | |

The distribution of the resulting light linear alkylbenzene, was the following:

| | % by weight |
|---|---|
| Phenyl C10 | 11.6 |
| Phenyl C11 | 36.5 |
| Phenyl C12 | 29.6 |
| Phenyl C13 | 21.6 |
| Phenyl C14 | 0.7 |
| 2 phenyl alkanes | 25.4 |

The effluent mixture as the resulting product from the alkylation reaction is subjected to conventional fractionation in distillation columns to separate its different component fractions. First of all, the benzene is separated as overhead distillation stream, in a column at a pressure of one atmosphere and temperature of 80° C. This benzene is the flow of recycled benzene, which is subsequently mixed with a small proportion of fresh benzene (5.6% of the total feed) to feed again the reactor. The rest of the reaction mixture is passed to another distillation column where, by head of the same and at a pressure of 100 mm Hg the n-paraffin current is separated. This stream is sent to the dehydrogenation unit to n-olefins prior to alkylation. Finally, the remaining fraction of alkyl-benzenes is subjected once again to fractionation in another distillation column separating on the top and at a pressure of 3 mm Hg, the light monoalkylbenzene (it includes the branched alkylbenzene) which is then stored, while in the bottom stream, the heavy alkylbenzene is separated (in turn, mixture approximately at 50% of dialkylbenzenes and diphenylalkanes) which is likewise sent to storage tanks.

The regeneration of the catalyst is carried out in a semicontinuous manner, making alternating and successive currents of paraffins and alcohols pass through the same in cycles lasting one hour for each product. The operating of the reactor continuously follows the following sequence:

Normal operating cycle: 12 hours

Catalyst regeneration cycle: 6 hours The temperature and liquid hourly space velocity of the solvent during the regeneration of the catalyst were, respectively, 220° C. and 1 hr$^{-1}$.

The mixture of solvents coming from the catalyst regeneration washing, which contains polymers as contaminants, is subjected to decantation in which on the one part (upper phase) the paraffins are separated and on the other part (lower phase) a mixture of alcohols, polymers and a certain percentage of paraffins (approximately 25% of the total volume of the phase) which has not been separated in the previous decantation. The polymers are separated from this mixture by drainage and the rest is subjected to a new fractionation in another distillation column where the alcohols are separated on top and the paraffins on the bottom, which are used again for regeneration of the catalyst by washing.

Example 2

Benzene is alkylated with $C_{10}$–$C_{14}$ detergent range linear olefins to produce linear monoalkylbenzene of an identical range in accordance with the process followed in Example 1 with the following exception: the benzene/olefin molar ratio of the feed have a value of 5, which is equivalent to a composition of the feed of 20% by weight of benzene and 80% by weight of paraffins and olefins.

The results shown in Table IV are obtained under these conditions:

| Conversion | 97.6% |
|---|---|
| (Bromine number at the entrance: 8.5) | 8.5) |
| (Bromine number at the outlet | 0.2) |
| Selectivity | |
| Linear alkylbenzene | 73% by weight |
| Branched alkylbenzene | 7% by weight |
| Heavy alkylbenzene | 20% by weight |
| Life of the catalyst (duration of the experiment): 300 hrs. (278 ml. of feed/g of catalyst) | |

Example 3

Benzene is alkylated with $C_{10}$–$C_{14}$ range linear olefins to produce linear monoalkylbenzene of an identical range in accordance with the process followed in Example 1 with the exception of the liquid hourly space velocity which takes the value of 2 hr$^{-1}$.

The results shown in Table V are obtained under these conditions.

TABLE V

| Conversion | 100% |
|---|---|
| Selectivity | |
| Linear alkylbenzene | 92% by weight |
| Branched alkylbenzene | 4% by weight |
| Heavy alkylbenzene | 4% by weight |
| Life of the catalyst (duration of the experiment): 300 hrs (278 ml. of feed/g of catalyst) | |

Example 4

Benzene is alkylated with $C_{10}$–$C_{14}$ detergent range linear olefins to produce monoalkylbenzene of an identical range.

The alkylation reaction is carried out continuously in a carbon steel tubular reactor with down flow, 330 mm long, with an inside diameter of 44.3 mm, an outside diameter of 45.4 mm and a height/inside diameter ratio of 7.45. The reactor is furnished with a thermowell to control the temperature, located at two third its height measured from the bottom. The heating of the feed and of the reactor is done by means of an electric tubular furnace; the reactor likewise having pressure, flow and temperature control mechanisms.

540 g of catalyst which occupy a volume of 500 cm³ are introduced in this reactor and placed in the form of a fixed bed. The catalyst is the same as described in Example 1. The feed to the reactor is also identical to that referred to in Example 1.

The operating conditions of the process are shown in Table VI.

TABLE VI

| | |
|---|---|
| Benzene/olefin molar ratio | 20 |
| Pressure | 35 kg/cm² |
| Temperature | 190° C. |
| Liquid hourly Space velocity | 4 hr⁻¹ |

The results shown in Table VII are obtained under these conditions:

TABLE VII

| | |
|---|---|
| Conversion | 95% |
| Selectivity | |
| Linear alkylbenzene | 91.7% by weight |
| Branched alkylbenzene | 6.3% by weight |
| Heavy alkylbenzene | 2.0% by weight |
| Life of the catalyst (duration of the experiment): 400 hrs (1,482 ml of feed/g of catalyst) | |

The effluent mixture as product resulting from the alkylation reaction is separated into its different component fractions in the same way as described in Example 1.

The regeneration of the catalyst is carried out semi-continuously, making alternating and successive streams, of a mixture of $C_{10}$–$C_{14}$ detergent range paraffins first and, on second, of alcohols, pass through the same, in cycles lasting one hour per product.

The cyclical sequence of the operation of the reactor continuously is the one indicated in Example 1 and the treatment of the mixture of solvents coming from the catalyst reeneration washing is also identical.

The temperature and liquid hourly space velocity of the solvents during the regeneration of the catalyst were, respectively, 190° C. and 4 hr⁻¹.

Example 5

Benzene is alkylated with $C_{10}$–$C_{14}$ range linear olefins to produce linear monoalkylbenzene of an identical range in accordance with the process followed in Example 4, with the following exception: the particle size of the catalyst is from 0.4–1.0 mm and the reaction temperature of the process is 170° C.

The results shown in Table VIII were obtained under these conditions:

TABLE VIII

| | |
|---|---|
| Conversion | 97.0 |
| Selectivity | |
| Linear alkylbenzene | 92.4% by weight |
| Branched alkylbenzene | 5.7% by weight |
| Heavy alkylbenzene | 1.9% by weight |
| Life of the catalyst (duration of the experiment): 182 hrs (673 ml of feed/g of catalyst) | |

We claim:

1. A continuous process for alkylating aromatic alcohols comprising:
   (a) reacting in a fixed-bed catalytic reactor and in the liquid phase a mixture of (i) at least one aromatic alcohol starting material and (ii) an alkylation agent, to obtain a product stream comprising at least one alkylated aromatic alcohol product, said reacting taking place:
   at a molar ratio of (i) to (ii) within the range of about 30:1 to 1:1;
   at a temperature within the range of about 100° to about 300° C.;
   at a pressure within the range of about 5 to 50 kg/cm² and a liquid hourly space velocity within the range of about 0.5 to about 20 hr⁻¹;
   in the presence of an alkylation catalyst comprising at least one solid selected from the group consisting of natural zeolites, synthetic zeolites, and clays, said solid comprising at least one of aluminum silicate and magnesium silicate and having:
   a surface area higher than about 80 m²/g;
   a microporosity higher than about 0.2 cm³/g;
   pores at least a majority of which have a diameter of less than about 60 A and an average diameter less than about 50 A;
   a percentage of meso and macropores within the range of about 10 to about 25% of total pores; said meso and macropores having a diameter higher than 60 A;
   said solid having been dried at a temperature within the range of about 60° to about 120° C. and calcined at a temperature within the range of about 200° and about 600° C.;
   (b) subjecting said product stream to a separation step to obtain (i) a fraction containing said at least one aromatic alcohol starting material; (ii) a fraction containing said at least one alkylated aromatic alcohol product in substantially pure form; (iii) a heavy alkylaromatic alcohol fraction; and (iv) a paraffin fraction.

2. The process of claim 1 further comprising periodically regenerating said catalyst by contacting said catalyst with streams of at least one paraffin alternating with streams of at least one alcohol, in cycles lasting for a period of time within the range of about 2 to about 8 hours at a temperature within the range of about 150° to about 300°. C. and at a liquid hourly space velocity of 1 to 10 hr⁻¹.

3. A process according to claim 1, wherein said regenerating step is performed periodically during said alkylating process.

4. A process according claim 3, wherein the aromatic alcohol is phenol.

5. The process of claim 3, wherein the alkylation agent is selected from the group of olefins, alkyl halides, alcohols, esters, ethers and acetylene hydrocarbons.

6. The process of claim 5, wherein the olefins comprise linear monolefins having from 2 to 20 carbon atoms.

7. The process of claim 6, wherein the olefins have from 8 to 16 carbon atoms.

8. The process of claim 3, wherein the alkylation catalyst is selected from the group of faujasite, clinoptilolite, mordenite, chabazite, eryonite, kaolinite, sepiolite, paligorskite, bentonite, montmorrillonite, hectorite, saponite, chlorite, ylite and halloysite.

9. The process of claim 3, wherein the alkylation catalyst is smectite.

10. The process of claim 3, wherein, said molar ratio is within the range of between 25:1 and 1:1.

11. The process of claim 10, wherein said molar ratio is within the range of between 20:1 and 1:1.

12. The process of claim 3, wherein said alkylation agent is diluted with paraffins at a paraffins/alkylation agent ratio (by weight) within the range of between 16:4 and 19:1.

13. The process of claim 12, wherein paraffins/alkylation agent ratio is within the range of between 17:3 and 19:1.

14. The process of claim 3, wherein the reacting step is carried out at a temperature within the range of 180°–230° C., a pressure within the range of 15–40 Kg/cm$^2$ and a liquid hourly space velocity within the range of 0.5 to 4.0 hr$^{-1}$.

15. The process of claim 3, wherein the alkylation catalyst used has a specific surface area higher than 100 m$^2$/g and has been dried at 100°–110° C. and calcined at 300°–500° C.

16. The process of claim 9, wherein the alkylation catalyst used has a specific surface area higher than 100 m$^2$/g and has been dried at 100°–110° C. and calcined at 300°–500° C.

17. The process of claim 9, wherein the alkylation catalyst used has a specific surface area higher than 100 m$^2$/g and has been dried at 100°–110° C. and calcined at 300°–500° C.

18. The process of claim 3, wherein the alkylation catalyst, also comprises at least one member selected from the group consisting of diatomaceous earth, perlite, silica and alumina.

19. A process of claim 3, wherein the alkylation catalyst has been modified for the purpose of strengthening its catalytic activity by ion exchange of the catalyst using salts of the cations selected from the group of Al$^{3+}$, Cr$^{3+}$, H$^+$, rare earth NH$_4^+$, Fe$^{3+}$, Co$^{3+}$, Ga$^{3+}$, Ni$^{2+}$ and Cu$^{2+}$.

20. A process of claim 3, wherein the alkylation catalyst has been modified or the purpose of strengthening its catalytic activity by treatment with at least one acid selected from the group of sulfuric, nitric, hydrochloric, perchloric, phosphoric, hydrofluoric, acetic, formic, propionic, oxalic and benzoic acid.

21. A process of claim 3, wherein the alkylation catalyst has been modified for the purpose of strengthening its catalytic activity by impregnation with at least one acid selected from the group consisting of sulfuric, nitric, hydrochloric, perchloric, phosphoric, hydrofluoric, acetic, formic, propionic, oxalic and benzoic acid or with at least one fluoride salt or with at least one salt of at least one metal selected from the group of aluminum, chrome, manganese, molybdenum, wolfram and rare earths.

22. The process of claim 3, wherein said alkylation catalyst has been formed using binders consisting of metallic oxides or hydroxides.

23. The process of claim 8, wherein said alkylation catalyst has been formed using binders consisting of metallic oxides or hydroxides.

24. The process of claim 9, wherein said alkylation catalyst has been shaped by binders consisting of metallic oxides or hydroxides.

25. The process of claim 22, wherein said metallic oxides or hydroxides are selected from the group consisting of aluminum oxide, silica-alumina and natural clays.

26. The process of claim 23, wherein said metallic oxides or hydroxides are selected from the group consisting of aluminum oxide, silica-alumina and natural clays.

27. The process of claim 24, wherein said metallic oxides or hydroxides are selected from, the group consisting of aluminum oxide, silica-alumina and natural clays.

28. The process of claim 3, wherein the regeneration of the catalyst is carried out at a temperature of 180°–230° C. and a liquid hourly space velocity of 1–4 hr$^{-1}$.

* * * * *